US006540980B1

(12) United States Patent
Blumenthal et al.

(10) Patent No.: US 6,540,980 B1
(45) Date of Patent: Apr. 1, 2003

(54) METHOD OF DETECTING ENDOMETRIOSIS

(75) Inventors: Rosalyn D. Blumenthal, Belleville, NJ (US); David M. Goldenberg, Mendham, NJ (US); Michael Samoszuk, Rancho Santa Margarita, CA (US)

(73) Assignee: Center for Molecular Medicine and Immunology, Belleville, NJ (US)

( * ) Notice: Subject to any disclaimer, the term of this patent is extended or adjusted under 35 U.S.C. 154(b) by 0 days.

(21) Appl. No.: 09/541,030

(22) Filed: Mar. 31, 2000

Related U.S. Application Data
(60) Provisional application No. 60/127,477, filed on Apr. 2, 1999.

(51) Int. Cl.$^7$ ................................................ A61B 49/00
(52) U.S. Cl. ..................... 424/9.34; 424/9.1; 424/1.11; 424/1.65; 424/9.3; 424/1.49
(58) Field of Search ................................. 206/569, 570; 424/1.11, 1.65, 1.49, 9.1, 9.3, 9.4, 9.5, 9.6, 9.34

(56) References Cited

U.S. PATENT DOCUMENTS

| | | | | | |
|---|---|---|---|---|---|
| 4,782,840 | A | * | 11/1988 | Martin, Jr. et al. | 128/654 |
| 4,932,412 | A | * | 6/1990 | Goldenberg | 128/654 |
| 5,478,725 | A | * | 12/1995 | Lessey | 435/7.21 |
| 5,631,247 | A | | 5/1997 | Dodge | 514/177 |
| 5,831,035 | A | * | 11/1998 | Timms | 530/389.1 |
| 5,843,673 | A | * | 12/1998 | Sharpe-Timms | 435/7.1 |
| 5,856,341 | A | | 1/1999 | Bell et al. | 514/324 |

OTHER PUBLICATIONS

M. Samoszuk et al. "New marker for blood vessels in human ovarian and endometrial cancers." Clinical Cancer Research, Nov. 1996, vol. 2, No. 11, pp. 1867–1871.
M. Samoszuk et al. "Radioimmunodetection of degranulated human eosinophils in mice: a potential model for Imaging Hodgkin's disease and other pathologic conditions." Journal of Nuclear Medicine, Jan. 1991, vol. 32, No. 1, pp. 89–94, XP002156537.
H.S. Keeping et al. "Monoclonal antibody to rat uterine peroxidase and its use in identification of the Peroxidase as being of eosinophil origin." Biochimica et Biophysica Acta, Dec. 20, 1984, vol. 802, No. 3, pp. 399–406, XP000971511.
K.M. Skubitz et al., "Preparation and characterization of monoclonal antibodies to human neutrophil cathepsin G, lactoferrin, eosinophil peroxidase, and eosinophil major basic protein." Journal of Leukocyte Biology, AGU 1989, vol. 46, No. 2, pp. 109–118, XP000971423.
M.C. Perez et al., "Role of eosiniphils in uterine responses to estrogen." Biology of Reproduction, Jan. 1996, vol. 54, No. 1, pp. 249–254, XP000971428.

H. U. Bryant et al. "Pharmacologic profile of estrogen–induced uterine eosinophilia in the ovariectomized (OVX) rat." Pharmacologist, Bethesda, MD., US, vol. 34, No. 3, Aug. 18, 1992, p 318 xp000971363.
M.F. Press et al., "Distribution of peroxidase and granulocytes in the human uterus", Laboratory Investigation, vol. 54, No. 2, 1986, pp. 188–203, XP000971137.
M.A. Mena et al., "Inhibition of non–genomic responses to estrogen in the rat uterus by testosterone propionate" Journal of Reproduction and Fertility, vol. 74, No. 1, 1985, pp. 1–8, XP000971132.
M.T. McMaster et al., "Activation and distribution of inflammatory cells in the mouse uterus during the preimplantation period" Journal of Immunology, vol. 148, No. 6, 1992, pp. 1699–1705, XP002156538.
B. A. Khaw et al., "Of Antimyosin Imaging and Histopathology of Myocardial Infarction: When, Where, and Why?", The Journal of Nuclear Medicine, vol. 32, No. 5, pp. 867–870, 1991.
Donald G. Mitchell et al., "Polycystic Ovaries: MR Imaging[1.]", Radiology, vol. 160, No. 2, pp. 425–429, 1986.
Marlene Zawin et al., "Endometriosis: Appearance and Detection at MR Imaging[1.]", Radiology, vol. 171, pp. 693–696, 1989.
Lionel arrive et al., "Pelvic Endometriosis: MR Imaging[1.]", Radiology, vol. 171, pp. 687–692, 1989.
W. Paul Dmowski et al., "Changing trends in the diagnosis of endometriosis: a comparative study of women with pelvic endometriosis presenting with chronic pelvic pain or infertility.", Fertility and Sterility, vol. 67, pp. 238–243, 1997.
Robert S. Schenken et al., "New Developments in Diagnostic Techniques.", Progress in Clinical and Biological Research, vol. 323, pp. 137–148, 1989.
D. M. Goldenberg et al., "Biological and clinical perspectives of cancer imaging and therapy with radiolabeled antibodies.", Seminars in Cancer Biology, vol. 1, pp. 217–225, 1990, W. B. Saunders Company.
D. M. Goldenberg, "Monoclonal Antibodies in Cancer Detection and Therapy.", The American Journal of Medicine, vol. 94, pp. 297–312, 1993.
James L. Murray, "Factors for Improving Monoclonal–Antibody Targeting.", Diagnostic Oncology, vol. 2, pp. 234–241, 1992.

(List continued on next page.)

Primary Examiner—Dameron L. Jones
(74) Attorney, Agent, or Firm—Foley & Lardner

(57) ABSTRACT

Kits for detecting and treating endometriosis are provided, which contain a targeting molecule comprising an eosinophil peroxidase-binding component. Methods of detecting and treating endometriosis using eosinophil peroxidase-specific targeting molecules are also provided Targeting molecules comprise an eosinophil peroxidase-binding component and an accessory component; the accessory component comprising an agent conferring detectability or a therapeutic effect.

6 Claims, No Drawings

OTHER PUBLICATIONS

Steven M. Larson, "Clinical Radioimmunodetection, 1978–1988: Overview and Suggestions for Standardization of Clinical Trials[1].", Cancer Research (Suppl.), vol. 50, pp. 892–898, 1990.

Steven M. Larson, "Clinical Radioimmunodetection, 1978–1988: Overview and Suggestions for Standardization of Clinical Trials[1].", Cancer Research (Suppl.), vol. 50, pp. 892–898, 1990.

Z. H. Oster et al., "Thrombus radioimmunoscintigraphy: An approach using monoclonal antiplatelet antibody.", Proceedings of the National Academy of Science, vol. 82, pp. 3465–3468, May 1985, Medical Sciences.

J. TH. Locher et al., "Imaging of inflammatory and infectious lesions after injection of radioiodinated monoclonal anti–granulocytes antibodies.," Nuclear Medicine Communications, vol. 7, pp. 659–670, 1986.

S. H. Kennedy et al., "Immunoscintigraphy of endometriosis.", British Journal of Obstetrics and Gynaecology, vol. 97, pp. 667–670, Aug., 1990.

Stephen Kennedy et al., "Imaging of pulmonary endometriosis by immunoscintigraphy. Case report.", British Journal of Obstetrics and Gynaecology, vol. 98, pp. 600–601, Jun. 1991.

R. F. P. M. Kruitwagen et al., "Immunocytochemical markerprofile of endometriotic epithelial, endometrial epithelial, and mesothelial cells: a comparative study.", European Journal of Obstetrics, Bynecology and Reproductive Biology: in press, vol. 19, pp. 51–64, 1992.

Michael Samoszuk et al., "Eosinophil Peroxidade Is Detectable with a Monoclonal Antibody in Collagen Bands of Nodular Sclerosis Hodgkin's Disease.", Laboratory Investigation, vol. 56, No. 4, pp. 394–400, 1987.

Michael K. Samoszuk et al., "Cytophilic and Cytotoxic Properties of Human Eosinophil Peroxidase Plus Major Basic Protein.", American Journal of Pathology, vol. 132., No. 3, pp. 455–460, Sep. 1988.

Michael Samoszuk et al., "Radioimmunodetection of Hodgkin's Disease and Non–Hodgkin's Lymphomas with Monoclonal Antibody to Eosinophil Peroxidase.", The Journal of Nuclear Medicine, vol. 34, No. 8, pp. 1246–1253, Aug., 1993.

Michael Samoszuk et al., "New Marker for Blood Vessels in Human Ovarian and Endometrial Cancers[1].", Clinical Cancer Research, vol. 2, pp. 1867–1871, Nov. 1996.

Michael Samoszuk et al., "Eosinophils and human cancer.", Histology and Histopathology, vol. 12, pp. 807–812, 1997, Jimenez Godoy, S.A.

Maria Jeziorska et al., "Mast Cell and Eosinophil Distribution and Activation in Human Endometrium throughout the Menstrual Cycle[1].", Biology of Reproduction, vol. 53, pp. 312–320, 1995.

Jost Brokelmann et al., "The Localization of Endogenous Peroxidase in the Rat Uterus and its Induction by Estradiol[1].", Biology of Reproduction, vol. 1, pp. 59–71, 1969.

Yon H. Lee et al., "Estrogen Regulation of an Eosinophil Chemotactic Factor in the Immature Rat Uterus.", Endocrinology, vol. 125, pp. 3022–3028, 1989.

Maria C. Leiva et al., "Ontogeny of the Production of an Estrogen–Regulated Eosinophil Chemotactic Factor in the Rat Uterus[1].", Biology of Reproduction, vol. 45, pp. 818–823, 1991.

Takao Fujisawa et al., "IL–5 as a Strong Secretagogue for Human Eosinophils.", International Archives of Allergy and Immunology, vol. 114 (Suppl.), pp. 81–83, 1997.

Huanzhong Shi et al., "Infiltration of Eosinophils into the Asthmatic Airways Caused by Interleukin 5.", American Journal of Respiratory Cell and Moleculare Biology, vol. 16, pp. 220–224, 1997.

* cited by examiner

METHOD OF DETECTING ENDOMETRIOSIS

CROSS REFERENCE TO RELATED APPLICATIONS

This application claims benefit of U.S. provisional application No. 60/127,477, filed Apr. 2, 1999.

The work in this application was supported in part by United States Public Health Services grant CA39841 from the National Institutes of Health.

BACKGROUND OF THE INVENTION

Endometriosis, the ectopic implantation of endometrial glands and stroma in regions remote from the uterine cavity, affects approximately 15% of women in their 30's–40's and is the cause of 35–45% of female infertility cases. Some women remain asymptomatic while others experience chronic pain. Mitchell in Endometriosis: Contemporary Concepts and Clinical Managment. (Schenker R, ed.: Lippincott, 1989). Endometriosis is usually confined to the pelvis, but extrapelvic sites have been reported in nearly all organs of the abdominal cavity. In addition, the thorax, skin, muscles, peripheral nerves, brain and spinal column are occasionally affected, as are surgical scars and the genital tract. Areas that are frequently involved include the abdominal wall, small intestines, appendix, urinary tract, and lymph nodes. Pauerstein, "Clinical presentation and diagnosis" in Endometriosis: Contemporary Concepts and Clinical Management (Schenker, ed. Lippincott 1989).

Methods to detect endometriosis have included: (a) serum immunoassays [CA-125, endometrial antibodies]; (b) imaging techniques [US, CT and MRI]; and (c) laparoscopic examination [reviewed by Pauerstein, supra]. Neither immunoassay approach is considered sufficiently sensitive. Barbieri, Fertil. Steril. 45:767–772 (1989); Chihal et al., Fertil. Steril. 46:408–420 (1986). Imaging approaches have met with varying degrees of success, with US and CT exhibiting the least sensitivity and specificity. Chihal et al., Fertil. Steril. 46:408–420 (1986); Fishman et al., J. Comput. Assist. Tomogr. 7:257–263 (1983).

MRI consistently demonstrates anatomic tissue planes, and has been useful for diagnosing several disorders of the female pelvis (Mitchell et al., Radiology 160:425–429 (1986)), however the signal intensity of endometriomas by MRI is very variable ranging from strong to relatively weak. MRI is useful for detecting the hemorrhagic masses due to a decrease in the signal intensity resulting from deoxyhemoglobin and hemosiderin. Other cysts cannot be distinguished from endometriomas (Zawin et al., Radiology 171:693–697(1989)) and resolution is often weak if lesions are not of high density. Furthermore, small adhesions, important in staging, are not seen by MRI. In the most promising report, an MRI sensitivity of 71% and a specificity of 82% was noted for 88 evaluable endometriotic lesion. Zawin et al., supra. In another study, sensitivity, specificity, and accuracy were 64%, 60%, and 63%, respectively. MRI could not be used to accurately detect extra-ovarian endometrial adhesions, and intraperitoneal implants. Nor did results correlate with surgical assessment of severity. Arrive et al., Radiology 171:687–692 (1989).

The optimal diagnostic tool to date is laparoscopy, resulting in about 90% correct diagnosis. Dmowski et al., Fertil Steril 67:238–43 (1997). There are however, circumstances in which direct visualization is difficult or inaccurate, such as, minimal lesions, adhesions that obscure visualization, ovarian endometriomas, and atypical non-pigmented endometriosis. Schenken et al., Prog. Clin. Biol. Res. 323:137–148 (1990). It is not, however, unusual to find patients who are normal on laparoscopy, that present with severe disease less than one-year later. Id. The invasiveness of the procedure may also be limiting preventing repeat examination to monitor efficacy of therapy and/or recurrence. Hence a need for a better detection system is needed.

Radiolabeled antibodies are a class of imaging agents for the detection of sites of disease. Goldenberg et al., Semin. Cancer Biol. 1:217–25 (1990); Goldenberg, Am. J. Med. 94:297–312 (1993). Results with $^{131}$I-labeled intact IgG have shown a general sensitivity of 80–90%. Murray et al., Diag. Oncol. 2:234–241 (1992); Larson, Cancer Res. 50:892–898 (1990). A specific antibody conjugated with a short half-life radionuclide, might be useful for immunoimaging of endometriosis, as it has been for the detection of primary and metastatic tumor lesions. Although RAID was first developed to identify malignant tissue, other applications have resulted, such as imaging myocardial infarction (Khaw et al., J. Nucl. Med. 28:1671–1678 (1987)), thrombi (Oster et al., Proc. Natl Acad. Sci. 82:3465–3468 (1985)), inflammation (Locher et al., Nucl. Med. Comm. 7:659–660 (1986)), and atherosclerotic plaques (Khaw et al., J. Nucl. Med. 32:1005–1012 (1991)).

Two case reports using immunoscintigraphy to image endometriosis have been presented. Kennedy used $^{131}$I or $^{111}$In labeled OC-125 F(ab')$_2$ anti-CA-125 with 89% sensitivity and 33% specificity to detect pelvic and pulmonary sites. Kennedy et al., Br. J. Obstet. Gyn. 97:667–670 (1990); Kennedy et al., Br. J. Obstet. Gyn. 98:600–601 (1991). The poor specificity is due (in part) to the inappropriate selection of CA-125 as a marker for endometriosis, which although elevated in some endometriosis patients, is not considered appropriate for screening. Barbieri, supra. To apply the technology of radioimmunoscintigraphy to clinical endometriosis imaging, [1] A suitable antigen found on most/all endometriotic specimens, must be selected; [2] An antibody with specificity for this antigen must be available.

Several antibodies raised to normal human endometrium exist (e.g., ENDOM5, ENDOM7, NEND3) that cross-react with endometriosis, and thus offer promise in diagnostic and therapeutic applications. Kruitwagen et al., Eur. J. Obstet. Gyn. Reprod. Biol. 19:51–64 (1992). In addition, antibodies recognizing either epithelial glycoproteins or mucins (e.g., RS-7, MA-5) found in solid tumors also react with endometriosis. However, the lack of specificity of these two groups of antibodies renders them inappropriate for specific endometriosis targeting.

Thus, a need exists in the art for techniques useful in detecting endometriosis. These techniques would overcome the art-based deficiencies discussed above. In addition, there is a need for improved methods of treating endometriosis once it has been detected.

SUMMARY OF THE INVENTION

It is therefore an object of the invention to provide kits and methods for overcoming the above-listed deficiencies in the art. According to this object, a kit for detecting or treating endometriosis is provided. This kit generally contains targeting agent, which is composed of an eosinophil peroxidase-binding component and a diagnostic or therapeutic accessory component, depending on the diagnostic or therapeutic application. In one embodiment, the peroxidase-binding component can be an antibody or an antibody fragment. Where the accessory component is for diagnostic use, it may be a detectable label, like a radionuclide, a fluorescent marker or an enzyme. Where the accessory component is for therapy, it may be a cytoablative agent. In another embodiment, the targeting agent, instead of containing a diagnostic or therapeutic accessory component, is adapted to receive such a component.

Also according to this object, a method of diagnosing endometriosis is provided. In one aspect, this method entails contacting endometrial tissue with an agent that has an eosinophil peroxidase-binding component and a detectable label, and then detecting that agent. The peroxidase-binding component can be, for example, an antibody or an antibody fragment. The detectable label may be, for example, a radionuclide, a fluorescent label or an enzyme. In different embodiments, this method, in part or in whole, may be accomplished in vivo or ex vivo.

Also according to this object, a method of treating endometriosis is provided. This method involves administering to an endometriosis patient an effective amount of an agent made up of an eosinophil peroxidase-binding component and a cytoablative agent. The peroxidase-binding component may be an antibody, an antibody fragment or the like.

DETAILED DESCRIPTION OF THE INVENTION

Eosinophil Peroxidase (EPO) is an intracellular enzyme that is released from eosinophils as they degranulate. Samoszuk et al., Lab. Invest. 56:394–400 (1987). The chemical properties of the enzyme result in an unusually high net positive charge allowing it to adhere strongly to the surface of negatively-charged cells that are adjacent to degranulating eosinophils. Samoszuk et al., Am. J. Pathol. 132:455–460 (1988). Degranulating cells have been identified in many lymphomas, breast cancers, and some gynecologic cancers. Samoszuk et al., J. Nucl. Med. 34:1246–1253 (1993); Samoszuk et al., Clin. Cancer. Res. 2:1867–1871 (1996); Samoszuk, Histol. Histopathol. 12:807–812 (1997). In normal endometrium, eosinophil accumulation and degranulation occurs just prior to and during menstruation. Jeziorska et al., Biol. Reprod. 53:312–320 (1995). This process is regulated, at least in part by estradiol ($E_2$) (Kelenyi et al., Acta Acad Sci. Hung. 23:253–267 (1972); Brokelmann et al., Biol. Reprod. 1:59–71 (1969)), which regulates production of an eosinophil chemoattractor factor (Lee et al., Endocrinol. 125:3022–3028 (1989); Leiva et al., Biology Reprod. 45:818–823 (1991)).

With the exception of sinuses in patients with allergic responses and airways in asthmatics, no other normal tissues express EPO in any significant way. Thus, EPO could potentially provide the specificity needed for a targeted antigen. The present inventors have now discovered that EPO is expressed in human endometriosis specimens. Given that this enzyme is not expressed in most tissues, including normal endometrium, EPO provides a useful surrogate for the diagnosis of endometriosis and a viable target for ablative treatment of endometriosis.

Targeting Agents

The methods and kits of the invention rely on a targeting agent that has at least two components. One component is an eosinophil peroxidase-binding component, and the other component is an accessory component. The eosinophil peroxidase-binding component specifically binds to eosinophil peroxidase; it is the portion that provides the specificity to differentiate between normal tissue and endometriosis tissue. On the other hand, the accessory component varies, depending on the use of the targeting agent. If a detection-based (e.g., diagnostic) use is desired, the accessory component will be detectable. If a therapeutic method is desired, the accessory component will be cytoablative or otherwise therapeutic. In another aspect, the targeting agent is adapted to receive a detection or therapeutic agent.

The chemical constitution of the eosinophil peroxidase-binding component may vary, but each should specifically bind to eosinophil peroxidase. Accordingly, macromolecules, such as proteins, carbohydrates (e.g., lectins) and RNAs are preferred. Due to the well known ability to generate molecules capable of binding with a wide range of specificities, antibodies, antibody fragments, and the like, are particularly preferred. Both monoclonal and polyclonal antibodies may be prepared according to established methods in the art. The art is well versed in both recombinant and chemical methods (crosslinking) for generating such agents.

Antibodies include, but are not limited to polyclonal antibodies, monoclonal antibodies (mAbs), human, humanized or chimeric antibodies, single chain antibodies including single chain Fv (scFv) fragments, Fab fragments, $F(ab')_2$ fragments, fragments produced by a Fab expression library, epitope-binding fragments, and human or humanized forms of any of the above.

In general, techniques for preparing polyclonal and monoclonal antibodies as well as hybridomas capable of producing the desired antibody are well known in the art (Campbell, A. M., *Monoclonal Antibody Technology: Laboratory Techniques in Biochemistry and Molecular Biology*, Elsevier Science Publishers, Amsterdam, The Netherlands (1984); St. Groth et al., *J. Immunol. Methods* 35:1–21 (1980); Kohler and Milstein, *Nature* 256:495–497 (1975)), the trioma technique, the human B-cell hybridoma technique (Kozbor et al., *Immunology Today* 4:72 (1983); Cole et al., in *Monoclonal Antibodies and Cancer Therapy*, Alan R. Liss, Inc. (1985), pp. 77–96). Affinity of the antisera for the antigen may be determined by preparing competitive binding curves, as described, for example, by Fisher, Chap. 42 in: *Manual of Clinical Immunology*, second edition, Rose and Friedman, eds., Amer. Soc. For Microbiology, Washington, D.C. (1980).

Fragments or derivatives of antibodies include any portion of the antibody which specifically binds a tumor antigen. Antibody fragments specifically include $F(ab')_2$, Fab, Fab' and Fv fragments. These can be generated from any class of antibody, but typically are made from IgG or IgM. They may be made by conventional recombinant DNA techniques or, using the classical method, by proteolytic digestion with papain or pepsin. See CURRENT PROTOCOLS IN IMMUNOLOGY, chapter 2, Coligan et al, eds., (John Wiley & Sons 1991–92).

$F(ab')_2$ fragments are typically about 110 kDa (IgG) or about 150 kDa (IgM) and contain two antigen-binding regions, joined at the hinge by disulfide bond(s). Virtually all, if not all, of the Fc is absent in these fragments. Fab' fragments are typically about 55 kDa (IgG) or about 75 kDa (IgM) and can be formed, for example, by reducing the disulfide bond(s) of an $F(ab')_2$ fragment. The resulting free sulfhydryl group(s) may be used to conveniently conjugate Fab' fragments to other molecules, such as localization signals.

Fab fragments are monovalent and usually are about 50 kDa (from any source). Fab fragments include the light (L) and heavy (H) chain, variable ($V_L$ and $V_H$, respectively) and constant ($C_L$ $C_H$, respectively) regions of the antigen-binding portion of the antibody. The H and L portions are linked by one or more intramolecular disulfide bridges.

Fv fragments are typically about 25 kDa (regardless of source) and contain the variable regions of both the light and heavy chains ($V_L$ and $V_H$, respectively). Usually, the $V_L$ and $V_H$ chains are held together only by non-covalent interactions and, thus, they readily dissociate. They do, however, have the advantage of small size and they retain the same binding properties of the larger Fab fragments. Accordingly, methods have been developed to crosslink the $V_L$ and $V_H$ chains, using, for example, glutaraldehyde (or other chemical crosslinkers), intermolecular disulfide bonds (by incorporation of cysteines) and peptide linkers.

Other antibody derivatives include single chain antibodies (U.S. Pat. No. 4,946,778; Bird, Science 242:423–426 (1988); Huston et al., Proc. Natl. Acad. Sci. USA 85:5879–5883 (1988); and Ward et al., Nature 334:544–546 (1989)). Single chain antibodies are formed by linking the heavy and light chain fragments of the Fv region via an amino acid bridge, resulting in a single chain FV (scFv).

Derivatives also include "chimeric antibodies" (Morrison et al., *Proc. Natl. Acad. Sci.*, 81:6851–6855 (1984); Neuberger et al., *Nature*, 312:604–608 (1984); Takeda et al., *Nature*, 314:452–454 (1985)). These chimeras are made by splicing the DNA encoding a mouse antibody molecule of appropriate specificity with, for instance, DNA encoding a human antibody molecule of appropriate specificity. Thus, a chimeric antibody is a molecule in which different portions are derived from different animal species, such as those having a variable region derived from a murine mAb and a human immunoglobulin constant region. Recombinant molecules having a human framework region and murine complementarity determining regions (CDRs) also are made using well-known techniques. These are also known sometimes as "humanized" antibodies and they and chimeric antibodies or antibody fragments offer the added advantage of at least partial shielding from the human immune system. They are, therefore, particularly useful in therapeutic applications. Human antibodies can be made in transgenic animals.

Multispecific, including bispecific, antibodies are also contemplated as useful in the methods of the present invention. Preferred antibodies have a specific immunoreactivity to a marker substance of at least 60% and a cross-reactivity to other antigens or non-targeted substances of less than 35%.

Accessory Component

The accessory component of the targeting agent confers either detectability or therapeutic benefit. It may comprise detectable labels and therapeutics of many sorts, especially those effective in treating endometriosis, or it may be adapted to receive such a label or therapeutic. Such adaptations are well known in the art and include, for example, chlelators and sulfhydryl moieties. The use of such an adapter confers the ability to add the label or therapeutic to the targeting agent immediately prior to use. Such adaptors also include antibodies, antibody fragments, and the like that have specificity for a therapeutic or diagnostic agent. Thus, adaptors will beneficially be employed especially where the label or therapeutic is not storage-stable or when a pre-targeting approach to therapy is utilized.

The detection/therapeutic agents, which comprise the accessory component, include any of the following: (1) diagnostic or therapeutic radionuclides (e.g., alpha-, beta-, gamma-, positron-, x-ray- and fluorescence-emitters; electron- and neutron-capturing agents); (2) MRI image enhancers; (3) photoactivated dyes for detection or therapy; (4) cytotoxic agents (e.g., drugs, toxins, hormones, cytokines, hormone antagonists, receptor antagonists); (5) differentiation agents (e.g., vitamins, cytokines, autocrines, certain hormones and drugs).

Detectable labels and therapeutic markers have been described, for example, in Hansen et al., U.S. Pat. No. 3,927,193 and Goldenberg, U.S. Pat. Nos. 4,331,647, 4,348,376, 4,361,544, 4,468,457, 4,444,744, 4,460,459, 4,460,561, 4,624,846 and 4,818,709, the disclosures of all of which are incorporated herein by reference.

MRI image-enhancing agents are well known in the art and include, for example, Gadolinium, Iron, Manganese, Rhenium, Europium, Lanthanum, Holmium and Terbium cationic species.

Internal detection procedures include intraoperative, intravascular or endoscopic, including laparoscopic, techniques, both surgically invasive and non-invasive. Moreover, other methods are available to increase the target:background ratios of the detection or therapeutic agents, such as pre-targeting and biotin/avidin approaches, as described, for example, in Goodwin et al., U.S. Pat. No. 4,863,713; Goodwin et al., J. Nucl Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; Stickney et al., Cancer Res. 51:6650, 1991; and Yuan et al., Cancer Res. 51:3119, 1991; all incorporated herein in their entirety by reference.

Among the radionuclides useful in the present invention, gamma-emitters, positron-emitters, x-ray emitters and fluorescence-emitters are suitable for localization and/or therapy, while beta- and alpha-emitters and electron- and neutron-capturing agents also can be used for therapy.

Suitable radioisotopes for the present invention include: Astatine-211, Iodine-123, Iodine-125, Iodine-126, Iodine-131, Iodine-133, Bismuth-212, Bromine-77, Indium-111, Indium-113m, Gallium-67, Gallium-68, Ruthenium-95, Ruthenium-97, Ruthenium-103, Ruthenium-105, Mercury-107, Mercury-203, Rhenium-186, Rhenium-188, Tellurium-121m, Tellurium-122m, Tellurium-125m, Thulium-165, Thulium-167, Thulium-168, Technetium-99m, Fluorine-18, Silver-111, Platinum-197, Palladium-109, Copper-67, Phosphorus-32, Phosphorus-33, Yttrium-90, Scandium-47, Samarium-153, Lutetium-177, Rhodium-105, Praseodymium-142, Praseodymium-143, Terbium-161, Holmium-166, Gold-199, Cobalt-57, Cobalt-58, Chromium-51, Iron-59, Selenium-75, Thallium-201, and Yfterbium-169. Preferably the radioisotope will emit in the 10–5,000 kev range, more preferably 50–1,500 kev, most preferably 50–500 kev.

Isotopes preferred for internal detection include: Iodine-125, Iodine-123, Iodine-131, Indium-111, Technetium-99m and Gallium-67. Isotopes preferred for therapeutic use include: Iodine-125, Iodine-131, Rhenium-186, Rhenium-188, Bismuth-212, Silver-111, Platinum-197, Palladium-109, Copper-67, Phosphorus-32, Phosphorus-33, Yttrium-90, Scandium-47, Samarium-153, Lutetium-177, Rhodium-105, Praseodymium-142, Praseodymium-143, Terbium-161, Holmium-166, Gold-199 and Astatine-211. An exemplary preferred class includes Auger electron-emitters.

In another aspect, the accessory component may facilitate targeting boron atoms to tumor cells for effecting boron neutron capture therapy (BNCT). BNCT is a binary system designed to deliver ionizing radiation to the endometrium by neutron irradiation of endometrium-localized boron-10 atoms. Thus, an exemplary method would involve pre-targeting with a targeting agent having streptavidin as the accessory component. Then, a boron-containing compound conjugated to biotin is administered, which binds to the streptavidin localized at the endometrium. The localized boron may then be irradiated, thereby effecting endometrial ablation. Alternatively, a bispecific antibody localized on endometrial tissue would have a second binding site for a hapten-linked boron addend, analogously to BNCT of tumors.

Many drugs and toxins are known which have cytotoxic effects on cells. They are to be found in compendia of drugs and toxins, such as the Merck Index, Goodman and Gilman's: The Pharmacological Basis of Therapeutics, current edition (MacMillan Publishing), and the like, and in the references cited above. Any such drug can be conjugated to or loaded onto the antibody by conventional means well know in the art.

Examples of known cytotoxic agents listed in Goodman and Gilman's include taxol; nitrogen mustards, such as mechlorethamine, cyclophosphamide, melphalan, uracil mustard and chlorambucil; ethylenimine derivatives, such as thiotepa; alkyl sulfonates, such as busulfan; nitrosoureas, such as carmustine, lomustine, semustine and streptozocin; triazenes, such as dacarbazine; folic acid analogs, such as methotrexate; pyrimidine analogs, such as fluorouracil, cytarabine and azaribine; purine analogs, such as mercaptopurine and thioguanine; vinca alkaloids, such as vinblastine and vincristine; antibiotics, such as dactinomycin, daunorubicin, doxorubicin, bleomycin, mithramycin and mitomycin; enzymes, such as L-asparaginase; platinum coordination complexes, such as cisplatin; substituted urea, such as hydroxyurea; methyl hydrazine derivatives, such as procarbazine; adrenocortical suppressants, such as mitotane; hormones and antagonists, such as adrenocortisteroids (preunisone), progestins (hydroxyprogesterone caproate, medroprogesterone acetate and megestrol acetate), estrogens (diethylstilbestrol and ethinyl estradiol), antiestrogens (tamoxifen), and androgens (testosterone propionate and fluoxymesterone).

Drugs that interfere with intracellular protein synthesis can also be used in the methods of the present invention; such drugs are known to these skilled in the art and include puromycin, cycloheximide, and ribonuclease.

Toxins can also be used in the methods of the present invention. Toxins useful as therapeutics are known to those skilled in the art and include plant and bacterial toxins, such as, abrin, alpha toxin, diphtheria toxin, exotoxin, gelonin, pokeweed antiviral protein, ricin, and saporin. The artisan will recognize that toxins in their native form require a minimum of three different biochemical functions to kill cells: a cell binding function, a cytotoxic function, and a function to translocate the toxic activity into the cells. The toxins useful in the present invention are generally modified, as is known in the art, so that the cell binding domain is nonfunctional, due to partial or total deletion, for example. Hence, the rely on the targeting function conferred by the eosinophil binding-component for cell binding, and thus killing.

Other therapeutic agents useful in the present invention include anti-DNA, anti-RNA, anti-protein and anti-chromatin cytotoxic or antimicrobial agents.

The present invention also contemplates conjugation to dyes used, for example, in photodynamic therapy. The use of light and porphyrins in methods of the present invention is also contemplated and their use in cancer therapy has been reviewed by van den Bergh (Chemistry in Britain, May 1986, Vol. 22, pp. 430–437), which is incorporated herein in its entirety reference.

The accessory component may be attached to the eosinophil peroxidase-binding component by a variety of methods known in the art. Many of these methods are disclosed in the above-referenced U.S. Patents and Patent Applications. See also, Rayudu, op. cit.; and Childs et al., J. Nuc. Med., 26: 293 (1985). Any conventional method of radiolabeling which is suitable for labeling isotopes for in vivo use will be generally suitable for labeling detection agents according to the present invention.

In one embodiment, the accessory component is adapted to receive a label and/or a therapeutic. Non-limiting examples of such adaptations include the presence of at least one chelator or sulfhydryl moiety.

Pharmaceutical Compositions

Pharmaceutical compositions according to the invention comprise at least one targeting agent as described above. In addition, these compositions typically further contain a suitable pharmaceutical excipient. Many such excipients are known to the art and examples may be found in REMINGTON'S PHARMACEUTICAL SCIENCES, chapters 83–92, pages 1519–1714 (Mack Publishing Company 1990) (Remington's), which are hereby incorporated by reference. The choice of excipient will, in general, be determined by compatibility with the therapeutic agent(s) and the route of administration chosen. The inventive compositions may be formulated as a unit dose which will contain either a therapeutically effective dose or some fraction thereof.

Kits

The kits of the invention typically comprise a targeting agent, as described above, and instructions for use. The agent may be formulated as a pharmaceutical composition and may be labelled for treatment or detection of endometriosis. Where the accessory component of the targeting agent employs a label or therapeutic that is not storage-stable, the agent will be adapted to receive the label or therapeutic immediately before use, rather than being pre-bound or conjugated to the agent. Thus, in one aspect, a kit will comprise a targeting agent that is adapted to receive a label or therapeutic immediately prior to use. Such a kit may also include other reagents for attaching the label or therapeutic. The label or therapeutic may also be supplied in the kit, or it may be obtained separately. It is envisioned that the instructions for use will comprise an administratively approved package insert. The uses will generally be either therapeutic or diagnostic.

Methods

The therapeutic methods of the invention typically involve administering to a patient in need of treatment a therapeutically effective amount of a composition which comprises a therapeutic agent of the invention. The patient is usually human, but may be a non-human animal. A patient generally will be in need of treatment when suffering from endometriosis. A therapeutically effective amount is generally an amount sufficient to induce substantial improvement in the endometriosis patient, as judged by a skilled clinician. Such improvements include, regression of the endometriosis, improvements in patient-well being and other significant markers of treatment. These markers include the reduction of pain at the site of the lesion(s) and increased chance of fertility where the endometriosis previously prevented pregnancy.

The diagnostic methods of the invention generally involve contacting endometrial tissue with an inventive targeting agent and detecting the agent. The tissue may be contacted and the agent detected in situ or ex vivo, and in situ contacting with ex vivo detection is specifically contemplated. Thus, for example, these methods may be adapted to conventional techniques, like laparoscopy, and they may be implemented by ex vivo examination of endometrial tissue samples. The advantage of this latter implementation is that it may readily be automated, in the manner that Pap smears are beginning to be screened, for instance.

For example, a suitably radiolabeled targeting agent is administered with the intention of obtaining an image of the lesion. The method of the invention can be practiced with either scintigraphic or magnetic resonance imaging agents.

The scintigram is normally taken by a gamma imaging camera having one or more windows for detection of energies in the 50–500 keV range. Use of radioisotopes with higher energy, beta, or positron emissions would entail use of imaging cameras with the appropriate detectors, all of which are conventional in the art. The scintigraphic data can be stored in a computer for later processing.

Methods useful for internal detection and/or treatment of tumors and/or other lesions are disclosed in U.S. Pat. Nos. 4,782,840 and 4,932,412, the disclosures of which are incorporated herein by reference. The methods of the present invention can be used to enhance the methods disclosed in these references.

Magnetic resonance imaging (MRI) is effected in an analogous manner to scintigraphic imaging except that the imaging agents will contain magnetic resonance (mr) enhancing species rather than radioisotopes. It will be appreciated that the magnetic resonance phenomenon operates on a different principle from scintigraphy. Normally, the signal generated is correlated with the relaxation times of the magnetic moments of protons in the nuclei of the hydrogen atoms of water molecules in the region to be imaged.

The magnetic resonance image enhancing agent acts by increasing the rate of relaxation, thereby increasing the contrast between water molecules in the region where the imaging agent accretes and water molecules elsewhere in the body. However, the effect of the agent is to decrease both $T_1$, and $T_2$, the former resulting in greater contrast while the latter results in lesser contrast. Accordingly, the phenomenon is concentration-dependent, and there is normally an optimum concentration of a paramagnetic species for maximum efficacy. This optimal concentration will vary with the particular agent used, the locus of imaging, the mode of imaging, i.e., spin-echo, saturation-recovery, inversion-recovery and/or various other strongly $T_1$-dependent or $T_2$-dependent imaging techniques, and the composition of the medium in which the agent is dissolved or suspended. These factors, and their relative importance are known in the art. See, e.g., Pykett, Scientific American, 246, 78 (1982); Runge et al., Am. J. Radiol., 141, 1209 (1983).

The MRI image enhancing agent must be present in sufficient amounts to enable detection by an external camera, using magnetic field strengths which are reasonably attainable and compatible with patient safety and instrumental design. The requirements for such agents are well known in the art for those agents which have their effect upon water molecules in the medium, and are disclosed, inter alia, in Pykett, op. cit., and Runge et al., op. cit. The MRI scans are stored in a computer and the images processed analogously to the scintigraphic data.

The term "treating" in its various grammatical forms in relation to the present invention refers to preventing, curing, reversing, attenuating, alleviating, minimizing, suppressing or halting the deleterious effects of a disease state, disease progression, disease causative agent (e.g., bacteria or viruses) or other abnormal condition.

EXAMPLE 1

This example shows the usefulness of eosinophil peroxidase as a marker of, and therpapeutic target for, endometriosis.

Tissue. Fresh endometriosis tissue was supplied by the Eastern and Midwestern Divisions of the Cooperative Human Tissue Network (CHTN) of the National Disease Research Institute and by Dr. Alice Demoupolis (New York University, Department of Gynecologic Pathology). Fresh surgical specimens from CHTN were shipped overnight on ice in DMEM media. CHTN tissues are processed for paraffin embedding and samples from NYU come paraffin-embedded. Both are immunohistochemically stained with anti-EPO or an isotype-matched irrelevant IgG (Ag8). Some samples are also stained with antibodies to IL-5 or IL-5R or eosinophil attracting chemokines (e.g., RANTES, eotaxin) to further address mechanistically the regulation of expression of EPO.

Tissue Culture. Some tissues were dissected under sterile conditions and pieces are cultured in the DMEM media in which the tissue was shipped in (containing patient blood as a source of human eosinophils) for 24, 48, or 72 h alone or with 1 or 10 nM estradiol ($E_2$) or 1 or 10 nM Progesterone (P) or the combination of both steroids. At the end of the incubation, tissues were fixed in formalin, dehydrated, cleared and paraffin embedded as above.

Experimental. Fresh endometriosis tissue was dissected into ~1 mm$^3$ pieces under sterile conditions and incubated with 10 nM $E_2$ for 24 h to induce metaloproteinases. Bruner et al., J. Clin. Invest. 99:2851–2857 (1997). Tissues were then coated with sorbsan and implanted intraperitoneally by trochar into $E_2$-stimulated nude mice (8 week old female Taconic athymic mice). Mice were estrogenized with a 30 $\mu$l intramuscular injection of depo-estradiol (Upjohn) which lasts for 3–4 weeks. Tissue was removed at 3–4 weeks after implantation and EPO expression evaluated histologically and compared with the original tissue prior to transplant into mice Hematoxylin & Eosin Staining. Five micron section of paraffin-embedded tissue was stained with hematoxylin-eosin. Slides were fixed for 5 minutes in 2% buffered formaldehyde, washed with tap water and stained for 3 min in Harris' hematoxylin with acetic acid (Sigma HHS-32+4 ml glacial acetic acid/100 ml stain). The slides were then washed with distilled water, dipped 5 times in acid alcohol (1 liter of 70% ETOH+10 ml concentrated HCl), and washed again in DH$_2$O. Finally, the slides were dipped in ammonia water (1 liter tap water+3 ml of 28% ammonium hydroxide), washed in DH$_2$O, placed in eosin for 30 seconds (Sigma HT110-32) and washed one final time with DH$_2$O before air drying and coverslipping with Cytoseal 60 mounting media.

Immunohistochemistry. Sections were fixed with 95% EtOH for 10 minutes. Indirect immunoperoxidase staining was done by first washing slides rapidly with phosphate buffered saline (PBS), then washing twice for 5 minutes each with 5% horse serum in PBS (HS-PBS) to block nonspecific antibody (Ab) binding. Each section was then covered with 25 $\mu$l of primary antibody (10 $\mu$g/ml) for 1 hour in a humid chamber. Excess Ab was washed off with 5% HS-PBS. Sections were then covered with 25 $\mu$l of biotinylated second Ab (1:200 dilution of stock) and incubated for 45 minutes under humid conditions. The excess secondary Ab was removed by washing in 5% HS-PBS. Endogenous peroxidase is destroyed by flooding slides with 0.3% H$_2$O$_2$ in methanol (1 ml of 3% H$_2$O$_2$ in 9 ml MeOH). Sections were washed again in PBS, covered with 25 $\mu$l of avidin-biotin complex (ABC) and incubated under humid conditions for 45 minutes. Excess ABC was washed off and sections are finally covered with 100 $\mu$l DAB solution (a 1:1 solution of 1 mg/ml diaminoibenzidine in 1 ml Tris-buffer and 67 µl of 3% $H_2O_2$) for 15 minutes. Slides were then washed thrice with PBS and counterstained briefly with hematoxylin.

Qualitative Immunohistochemical Analysis. Reactivity of Ab with endometriosis sections was performed by determining the number that are positive/number tested. Reactivity is defined as follows: negative, <5% of tissue stained; −/+, <10% of the tissue stained; +1, stain of low intensity (<25%); 2+, 25–50% of tissue stained with moderate intensity; 3+, 50–75% of tissue stained intensely; and 4+>75% intensely stained. Staining patterns for individual specific tissue regions were evaluated: e.g., glandular epithelium, luminal secretions, and stroma.

Quantitative Immunohistochemical Analysis. A Bioquant-OS/2 video image analyzer with a high resolution 1024× 768 video camera and a 256 Grey scale level frame grabbing graphic board was used to generate reports containing measurements of areas of staining and optical density of stained area. This system of analysis is rapid, using an intel processor. Exact x,y,z topography is recorded during morphometry and accurate topography is maintained regardless of magnification. Multiple regions (3–5 depending on the size of the tissue) on each slide were evaluated.

Results: Staining intensity and uniformity was determined in fresh specimens obtained from The Cooperative Human Tissue Network (CHTN). Staining intensity and uniformity showed variability between specimens. However, 18/19 tissues demonstrated positive EPO expression in the connective tissue and on some blood vessels and 4 of these were very intense, while 7 were moderately intense. Some specimens even contained evidence of medusa cells, a connective tissue eosinophil that has assumed an ameboid or fibrillar shape. The fact that 95% of the samples tested were positive EPO expressors indicates that EPO will be a useful target for clinical targeting of endometriosis. Any variability observed may be a function of the stage of the menstrual cycle (steroid hormone levels). The results are presented in Table 1.

TABLE 1

Staining intensity of endometriosis tissue treated with labeled eosinophil peroxidase-specific antibody

| Staining Intensity | − | +/− | +1 | +2 | +3 | +4 |
|---|---|---|---|---|---|---|
| Number of specimens | 1 | 1 | 7 | 7 | 1 | 3 |

In an effort to understand the regulation of expression, the expression of IL-5 and its receptor in endometriosis has been further explored. Expression of various cytokines (e.g., IL-1, 2, 4, 5, 6, 8, 10, IFNγ, TNFα, GM-CSF) in peritoneal fluid of endometriosis patients has been studied (reviewed in Giuduce et al., J. Reprod. Med. 43:252–262 (1998)). Since, IL-5 is a strong chemo-attractant for eosinophils (Fujisawa et al., Int'l. Arch. Allergy Immunol. 114 Suppl. 1:81–83 (1997); Shi et al., Am. J. Respir. Cell Mol. Biol. 16:220–224 (1997)), immunohistochemistry (IHC) was performed to determine expression of IL-5 and its receptor in the same specimens. IL-5 expression was increased in 7/8 specimens studied (+1 intensity) and IL-5R was increased in 18/19 specimens (+1 to +3). The one sample that was negative for IL-5 and IL-5R was also negative for EPO suggesting that the IL-5 system may mediate the creation of the EPO target.

EXAMPLE 2

This example demonstrates coupling of $^{32}$P-AMP-1-(N-Maleimidomethyl) cyclohexane-4-(2-aminoethylacetamide) to anti-Eosinophil Peroxidase Antibody.

The antibody is reduced by addition of 2-mercaptoethanol at pH 8.7 for 10 min at 4° C. to produce two free thiol groups in the hinge region of the antibody. Reduced antibody is dissolved in sodium phosphate buffer (pH 6) and $^{32}$P-AMP-MCAA (0.5 eq.) is added. Progress of the reaction is monitored by size-exclusion chromatography on a BioSil 250 column (Biorad, Hercules, Calif.) using an in-line radiation detector.

EXAMPLE 3

This example demonstrates measuring the biodistribution of $^{32}$P-labeled antibody.

The conjugated antibody is injected into 35 BALB/c mice at a concentration of 10 mg/kg body weight. Five animals are sacrificed at each time point of 2 h, 4 h, 1,2,3,7, and 14 days. At each time point the mice are dissected to remove all bone tissue, which is solubilized in ethanol/nitric acid. Non-bone tissue is solubilized in TS-1 (Research Products International). Both solubilized samples are added to scintillation fluid and radioactivity measured using a scintillation counter. Bone and non-bone radioactivity is compared at each time point. Increased amounts of radioactivity found in bone indicates increased breakdown of the conjugate.

The foregoing detailed discussion and examples are presented for illustrative purposes only, and are not meant to be limiting. The skilled artisan will readily appreciate numerous aspects of the invention that are not specifically exemplified, yet are within the scope of the following claims.

We claim:

1. A method of diagnosing endometriosis, comprising contacting endometrial tissue with an agent which comprises an eosinophil peroxidase-binding component and a detectable label, and then detecting said agent.

2. A method according to claim 1, wherein said peroxidase-binding component is an antibody or an antibody fragment.

3. A method according to claim 2, wherein said detectable label is selected from the group consisting of a radioactive label, an MRI image enhancing agent, a fluorescent label and an enzyme.

4. A method according to claim 1, wherein said contacting is accomplished in vivo.

5. A method according to claim 1, wherein said detecting is accomplished ex vivo.

6. A method of treating endometriosis, comprising providing a patient in need of said treatment with an effective amount of an agent which comprises an eosinophil peroxidase-binding component and a cytoablative agent.

* * * * *